United States Patent
Woehl et al.

(12) 
(10) Patent No.: US 10,265,690 B2
(45) Date of Patent: Apr. 23, 2019

(54) CATALYST COMPOSITION AND PROCESS FOR OLIGOMERIZATION OF ETHYLENE

(71) Applicants: SAUDI BASIC INDUSTRIES CORPORATION, Riyadh (SA); LINDE AG, Munich (DE)

(72) Inventors: Anina Woehl, Munich (DE); Andreas Meiswinkel, Munich (DE); Heinz Boelt, Munich (DE); Bernd H. Mueller, Munich (DE); Wolfgang Mueller, Munich (DE); Normen Peulecke, Munich (DE); Uwe Rosenthal, Munich (DE); Marco Harff, Munich (DE); Mohammed H. Al-Hazmi, Riyadh (SA); Abdullah Alqahtani, Riyadh (SA)

(73) Assignees: SAUDI BASIC INDUSTRIES CORPORATION, Riyadh (SA); LINDE AG, Munich (DE)

( * ) Notice: Subject to any disclaimer, the term of this patent is extended or adjusted under 35 U.S.C. 154(b) by 0 days.

(21) Appl. No.: 15/379,836

(22) Filed: Dec. 15, 2016

(65) Prior Publication Data
US 2017/0128925 A1  May 11, 2017

Related U.S. Application Data

(62) Division of application No. 14/908,026, filed as application No. PCT/IB2014/063485 on Jul. 28, 2014, now Pat. No. 9,561,500.

(60) Provisional application No. 62/008,237, filed on Jun. 5, 2014.

(30) Foreign Application Priority Data

Jul. 29, 2013 (EP) .................... 13178362

(51) Int. Cl.
| | | |
|---|---|---|
| B01J 31/18 | (2006.01) | |
| B01J 31/14 | (2006.01) | |
| C07C 2/36 | (2006.01) | |
| C07C 2/32 | (2006.01) | |

(52) U.S. Cl.
CPC ......... *B01J 31/1885* (2013.01); *B01J 31/143* (2013.01); *C07C 2/32* (2013.01); *C07C 2/36* (2013.01); *B01J 2231/20* (2013.01); *B01J 2531/62* (2013.01); *C07C 2531/14* (2013.01); *C07C 2531/22* (2013.01); *C07C 2531/24* (2013.01); *Y02P 20/52* (2015.11)

(58) Field of Classification Search
None
See application file for complete search history.

(56) References Cited

U.S. PATENT DOCUMENTS

| 7,323,611 B2 | 1/2008 | Nabika |
|---|---|---|
| 2006/0173226 A1 | 8/2006 | Blann et al. |
| 2006/0229480 A1 | 10/2006 | Blann et al. |
| 2007/0232481 A1 | 10/2007 | Zhang et al. |
| 2016/0167033 A1 | 6/2016 | Woehl et al. |

FOREIGN PATENT DOCUMENTS

| CA | 2765429 | * | 7/2013 | ................ C07F 9/50 |
|---|---|---|---|---|
| EP | 2106854 A1 | | 10/2009 | |
| EP | 2489431 | * | 8/2012 | .............. B01J 31/14 |
| EP | 2167231 B1 | | 9/2012 | |
| EP | 2832445 A1 | | 4/2015 | |
| WO | 0204119 A1 | | 1/2002 | |
| WO | 03053891 A1 | | 7/2003 | |
| WO | 2008077908 A1 | | 7/2008 | |
| WO | 2009006979 A2 | | 1/2009 | |
| WO | 2010115520 A1 | | 10/2010 | |
| WO | 2015015402 A2 | | 2/2015 | |

OTHER PUBLICATIONS

Babu et al. (Proc. Indian Acad. Sci. (Chem. Sci.), 106(1), 1994, 37-43). (Year: 1994).*
Chinese Office Action for application No. 2014800425349 dated Jul. 14, 2017, 11 pages. (SL30019CN).
International Preliminary Report on Patentability, International Application No. PCT/IB2014/063485, International Filing Date—Jul. 28, 2014, Date of Issuance Feb. 2, 2016, 11 pages; (SL30019PCT).

* cited by examiner

*Primary Examiner* — Yun Qian
(74) *Attorney, Agent, or Firm* — Cantor Colburn LLP

(57) ABSTRACT

A catalyst composition including: (a) a chromium compound; (b) a ligand of the general structure $R_1R_2P-N(R_3)-P(R_4)-NR_5R_6$ or    (A)

$R_1R_2P-N(R_3)-P(XR_7)R_8$ or $R_1R_2P-N(R_3)-P(XR_7)_2$, with $X=O$ or $S$,    (B)

wherein $R_1$, $R_2$, $R_3$, $R_4$, $R_5$, $R_6$, $R_7$ and $R_8$ are independently $C_1$-$C_{10}$-alkyl, $C_6$-$C_{20}$-aryl, $C_3$-$C_{10}$-cycloalkyl, aralkyl, alkylaryl, or trialkylsilyl, or any cyclic derivatives of (A) and (B), wherein at least one of the P or N atoms of the PNPN-unit or PNP-unit is a member of the ring system, the ring system being formed from one or more constituent compounds of structures (A) or (B) by substitution; and (c) an activator or co-catalyst; and a process for tri- and/or tetramerization.

13 Claims, No Drawings

CATALYST COMPOSITION AND PROCESS FOR OLIGOMERIZATION OF ETHYLENE

PRIORITY

This application is a Divisional of U.S. patent application Ser. No. 14/908,026 filed Jan. 27, 2016, entitled "CATALYST COMPOSITION AND PROCESS FOR OLIGOMERIZATION OF ETHYLENE"; which is a National Stage application of International Application No. PCT/IB2014/063485, filed Jul. 28, 2014; which claims the benefit of U.S. Provisional Application No. 62/008,237, filed Jun. 5, 2014 and EP Application No. 13178362.3, filed Jul. 29, 2013, the contents of which are incorporated by reference in their entirety.

BACKGROUND

The present invention relates to a catalyst composition and a process for the oligomerization, especially tri- and tetramerization, of ethylene.

Existing processes for the production of linear alpha olefins (LAOs), including comonomer-grade 1-hexene and 1-octene, rely on the oligomerization of ethylene. These processes have in common that they lead to a product distribution of ethylene-oligomers of chain length 4, 6, 8 and so on. This is due to a chemical mechanism which is widely governed by competing chain growth- and displacement reaction steps, leading to a Schulz-Flory- or Poisson-product distribution.

From the marketing point of view, this product distribution poses a formidable challenge for the full-range alpha olefins producer. The reason is that each market segment served exhibits a very different behavior in terms of market size and growth, geography, fragmentation etc. It is, therefore, very difficult for the producer to adapt to the market requirements since part of the product spectrum might be in high demand in a given economic context, while at the same time other product cuts might not be marketable at all or only in a marginal niche. Currently, the highest-value LAO product is comonomer-grade 1-hexene for the polymer industry, while 1-octene demand is also growing at a considerable rate.

WO 2009/006979 A2 describes a catalyst composition and a process for the di-, tri- and/or tetramerization of ethylene. The catalyst composition comprises a chromium compound, a ligand of, for example, the general structure $R_1R_2P$—$N(R_3)$—$P(R_4)$—$N(R_5)$—$H$ and a co-catalyst acting as an activator. The ligand's substituents $R_1$, $R_2$, $R_3$, $R_4$ and $R_5$ are independently a number of functional groups, comprising (among others) $C_1$-$C_{10}$-alkyl, aryl and substituted aryl.

The chromium source is $CrCl_3(THF)_3$, Cr(III)acetylacetonate, Cr(III)octanoate, Cr-hexacarbonyl, Cr(III)-2-ethylhexanoate and (benzene)tricarbonyl-chromium (THF=tetrahydrofuran).

The co-catalyst or activator is trimethylaluminum, triethylaluminum, triisopropylaluminum, triisobutylaluminum, ethylaluminumsesquichloride, diethylaluminum chloride, ethylaluminumdichloride, methylaluminoxane or a combination comprising at least one of the foregoing.

This prior art discloses a class of catalyst systems for selective ethylene oligomerization reactions.

For example, one embodiment uses a specific catalyst composition, chosen from this class of catalyst systems, for the highly selective trimerization of ethylene to afford high yields of 1-hexene.

This choice of catalyst constituents comprises $CrCl_3(THF)_3$ as chromium source, triethylaluminum as activator, and $(Ph)_2P$—$N(i\text{-Pr})$—$P(Ph)$-$N(i\text{-Pr})$—$H$ as ligand for the catalytically active complex (Ph=phenyl group, i-Pr=isopropyl group). This ligand features the typical PNPN—H-backbone, which is why this class of compounds, regardless of the precise nature of its substituents, is often referred to as a "PNPN—H-ligand".

WO 2010/115520 A1 describes essentially modified catalyst systems of the general type already disclosed in WO2009/006979 A2. These modified systems take advantage from the same PNPN—H-type ligands that were already known. However, now a "modifier" is added to the system, (but not limited to) ammonium or phosphonium salts of the type $[H_4E]X$, $[H_3ER]X$, $[H_2ER_2]X$, $[HER_3]X$ or $[ER_4]X$ (with E=N or P, X=Cl, Br or I and R=alkyl, cycloalkyl, acyl, aryl, alkenyl, alkynyl etc.).

Preferred embodiments involve, for instance, modifiers such as tetraphenylphosphonium chloride, tetraethylammonium chloride-monohydrate, triethylamine-hydrochloride etc. Also, as a "type $[ER_4]X$"-modifier, dodecyl trimethylammonium chloride can advantageously be used, due to its low price, abundant supply and good solubility in the reaction solution. By means of the halogen-containing modifier, the catalyst system allows for an independent adjustment of the [Cr]/[Halogen] molar ratio in the resulting catalytically active species which is formed in-situ under oligomerization conditions.

On technical scale, the prior art oligomerization technologies described above are mainly suitable for the production of 1-butene and 1-hexene for use as co-monomers in the polyethylene (PE) production, especially for linear low density polyethylene (LLDPE).

Currently, most of the co-monomer used for PE production is 1-butene followed by an increasing 1-hexene demand. However, some high-quality PE-materials featuring high tensile strength and crack resistance require 1-octene as co-monomer. So far, the largest quantity of 1-octene is obtained from full-range LAO-processes or extraction from Fischer-Tropsch streams. Since these technologies are burdened with rather big amounts of other products than 1-octene, their economic viability varies greatly with technological and economic boundary conditions. This pertains to infrastructure, market access and price development for the full-range products under the local boundary conditions.

It is, therefore, desirable to have catalyst systems and processes with a higher selectivity towards 1-octene available. Since 1-hexene is also a valuable co-monomer, combined 1-hexene/1-octene processes are economically interesting as well.

SUMMARY

In an embodiment, a catalyst composition comprises:
(a) a chromium compound;
(b) a ligand of the general structure

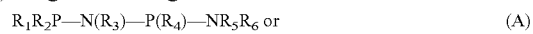

wherein $R_1$, $R_2$, $R_3$, $R_4$, $R_5$, $R_6$, $R_7$ and $R_8$ are independently $C_1$-$C_{10}$-alkyl, $C_6$-$C_{20}$-aryl, $C_3$-$C_{10}$-cycloalkyl, aralkyl, alkylaryl, or trialkylsilyl, or any cyclic derivatives of (A) and (B), wherein at least one of the P or N atoms of the PNPN-unit or PNP-unit is a member of the ring system, the ring system being formed from one or more constituent compounds of structures (A) or (B) by substitution; and
(c) an activator or co-catalyst.

In another embodiment, a method of obtaining the catalyst comprises combining at least (a) a chromium compound; (b) a ligand of the general structure (A) or (B) as described above; and (c) an activator or co-catalyst.

In still another embodiment, a process for tri- and/or tetramerization of ethylene comprises subjecting the above-described catalyst composition to a gas phase of ethylene in a reactor and conducting an oligomerization.

DETAILED DESCRIPTION

Described herein is a catalyst composition and a process for oligomerization with a high selectivity towards 1-octene overcoming the disadvantages of the prior art. Especially a catalyst and process shall be provided, which allow production of 1-octene in higher selectivities, while processes having a combined production of 1-hexene/1-octene are also of interest. The catalyst composition comprises: (a) a chromium compound; (b) a ligand of the general structure

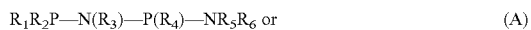

$R_1R_2P$—$N(R_3)$—$P(R_4)$—$NR_5R_6$ or (A)

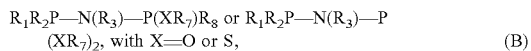

$R_1R_2P$—$N(R_3)$—$P(XR_7)R_8$ or $R_1R_2P$—$N(R_3)$—$P(XR_7)_2$, with X=O or S, (B)

wherein $R_1$, $R_2$, $R_3$, $R_4$, $R_5$, $R_6$, $R_7$ and $R_8$ are independently $C_1$-$C_{10}$-alkyl, $C_6$-$C_{20}$-aryl, $C_3$-$C_{10}$-cycloalkyl, aralkyl, alkylaryl, or trialkylsilyl, or any cyclic derivatives of (A) and (B), wherein at least one of the P or N atoms of the PNPN-unit or PNP-unit is a member of the ring system, the ring system being formed from one or more constituent compounds of structures (A) or (B) by substitution; and (c) an activator or co-catalyst.

As is to be understood, any cyclic derivatives of (A) and (B) can be utilized as ligand, wherein at least one of the P or N atoms of the PNPN-unit (structure (A)) or PNP-unit (structure (B)) is a ring member, the ring being formed from one or more constituent compounds of structures (A) or (B) by substitution, i.e. by formally eliminating per constituent compound either two whole groups $R_1$-$R_8$ (as defined) or H, one atom from each of two groups $R_1$-$R_8$ (as defined) or a whole group $R_1$-$R_8$ (as defined) or H and an atom from another group $R_1$-$R_8$ (as defined), and joining the formally so-created valence-unsaturated sites by one covalent bond per constituent compound to provide the same valence as initially present at the given site.

An example of such a cyclic derivative can be as follows.

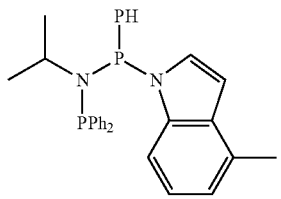

Preferably the chromium compound is organic or inorganic salts, coordination complexes and organometallic complexes of Cr(II) or Cr(III)

Most preferably the chromium compound is $CrCl_3(THF)_3$, Cr(III)acetylacetonate, Cr(III)octanoate, chromium hexacarbonyl, Cr(III)-2-ethylhexanoate, (benzene)tricarbonyl-chromium, or a combination comprising at least one of the foregoing.

It is also preferred that $R_1$, $R_2$, $R_3$, $R_4$, $R_5$, $R_6$, $R_7$ and $R_8$ are methyl, ethyl, isopropyl, tert-butyl, cyclohexyl, phenyl, benzyl, tolyl, xylyl, or a combination comprising at least one of the foregoing.

In one embodiment the activator or co-catalyst is trimethylaluminum, triethylaluminum, triisopropylaluminum, triisobutylaluminum, ethylaluminumsesquichloride, diethylaluminum chloride, ethylaluminumdichloride, methylaluminoxane (MMAO), modified methylaminoxane, or a combination comprising at least one of the foregoing.

Most preferred is a catalyst composition, wherein the ligand is $Ph_2P$—$N(i-Pr)$—$P(Ph)$-$N(i-Pr)Ph$, $Ph_2P$—$N(i-Pr)$—$P(Ph)$-$N(Me)C_6H_6$, $Ph_2P$—$N(i-Pr)$—$P(Ph)S(i-Pr)$, $Ph_2P$—$N(i-Pr)$—$P(Ph)OC_2H_5$, $Ph_2P$—$N(i-Pr)P(Ph)OCH_3$, or a combination comprising at least one of the foregoing.

A catalyst composition is also preferably provided additionally comprising a solvent, preferably aromatic hydrocarbons, straight-chain and cyclic aliphatic hydrocarbons, straight-chain olefins and ethers, preferably toluene, benzene, ethylbenzene, cumene, xylenes, mesitylene, hexane, octane, cyclohexane, methylcyclohexane, hexene, heptene, octene, diethylether, tetrahydrofuran, chlorobenzene, or a combination comprising at least one of the foregoing, most preferably toluene or chlorobenzene.

In one embodiment, the concentration of the chromium compound is from 0.01 to 100 mmol/l, preferably 0.1 to 10 mmol/l.

The ligand/Cr molar ratio is preferably from 0.5 to 50, preferably 0.8 to 2.0. The Al/Cr molar ratio preferably is from 1:1 to 1000:1, preferably 10:1 to 200:1.

As is obvious for someone skilled in the art, the components (a) to (c) for providing the catalyst composition are more or less considered as starting materials, but may be converted when the free compounds (a)-(c) are mixed to form the catalyst composition. In this regard, the catalyst composition according to the present invention can be also illustrated as being obtainable by combining at least (a) a chromium compound; (b) a ligand of the general structure

$R_1R_2P$—$N(R_3)$—$P(R_4)$—$NR_5R_6$ or (A)

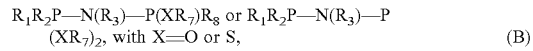

$R_1R_2P$—$N(R_3)$—$P(XR_7)R_8$ or $R_1R_2P$—$N(R_3)$—$P(XR_7)_2$, with X=O or S, (B)

wherein $R_1$, $R_2$, $R_3$, $R_4$, $R_5$, $R_6$, $R_7$ and $R_8$ are independently $C_1$-$C_{10}$-alkyl, $C_6$-$C_{20}$-aryl, $C_3$-$C_{10}$-cycloalkyl, aralkyl, alkylaryl, or trialkylsilyl or any cyclic derivatives of (A) and (B), wherein at least one of the P or N atoms of the PNPN-unit or PNP-unit is a member of the ring system, the ring system being formed from one or more constituent compounds of structures (A) or (B) by substitution; and (c) an activator or co-catalyst.

According to the invention is also a process for tri- and/or tetramerization of ethylene, comprising subjecting a catalyst composition according to the invention to a gas phase of ethylene in a reactor and conducting an oligomerization. Requirements and conditions for conducting an oligomerization using an organo metallic catalyst are well known in the art. Preferably the oligomerization is carried out at a pressure of 1 to 200 bar, preferably 10 to 50 bar.

Also preferred, the oligomerization is carried out at a temperature of from 10 to 200° C., preferably 20 to 100° C.

In one embodiment, the process is carried out continuously, semi-continuously or discontinuously.

Finally, the mean residence time may be from 10 minutes to 20 hours, preferably 1 to 4 hours.

Surprisingly, it was found that the inventive catalyst composition provides the oligomerization of ethylene with a significantly increased selectivity towards 1-octene and activity. It was further found that based on the prior art, the respective ligand structure can be successfully amended to increase the 1-octene selectivity. In a preferred embodiment, it was also found that the selectivity can be further increased with suitable co-catalysts and solvents which effect the control of the process overall selectivity.

Further advantages and features of the present invention are now illustrated in the following example section.

EXAMPLES

It was found that there are two substantial embodiments with regard to the ligand. In a first embodiment, a ligand having the structure $R_1R_2P-N(R_3)-P(R_4)-NR_5R_6$ is used. In a second embodiment, the ligand is $R_1R_2P-N(R_3)-P(XR_7)R_8$ or $R_1R_2P-N(R_3)-P(XR_7)_2$ with X=O or S. The ligands of the first embodiment are accessible via various synthetic approaches that are shown below.

Particular ligands of this first embodiment that were successfully synthesized are shown also below.

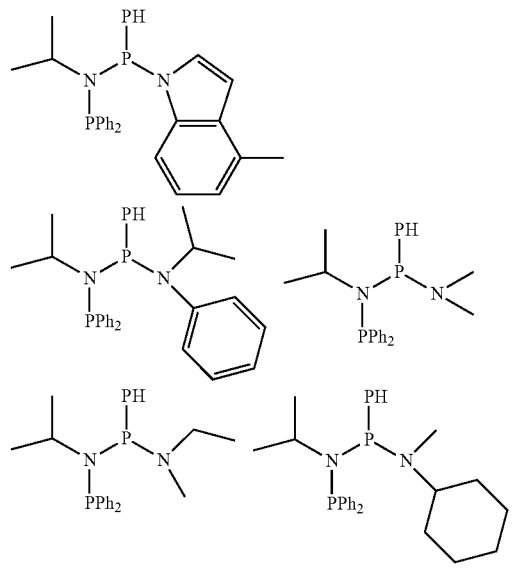

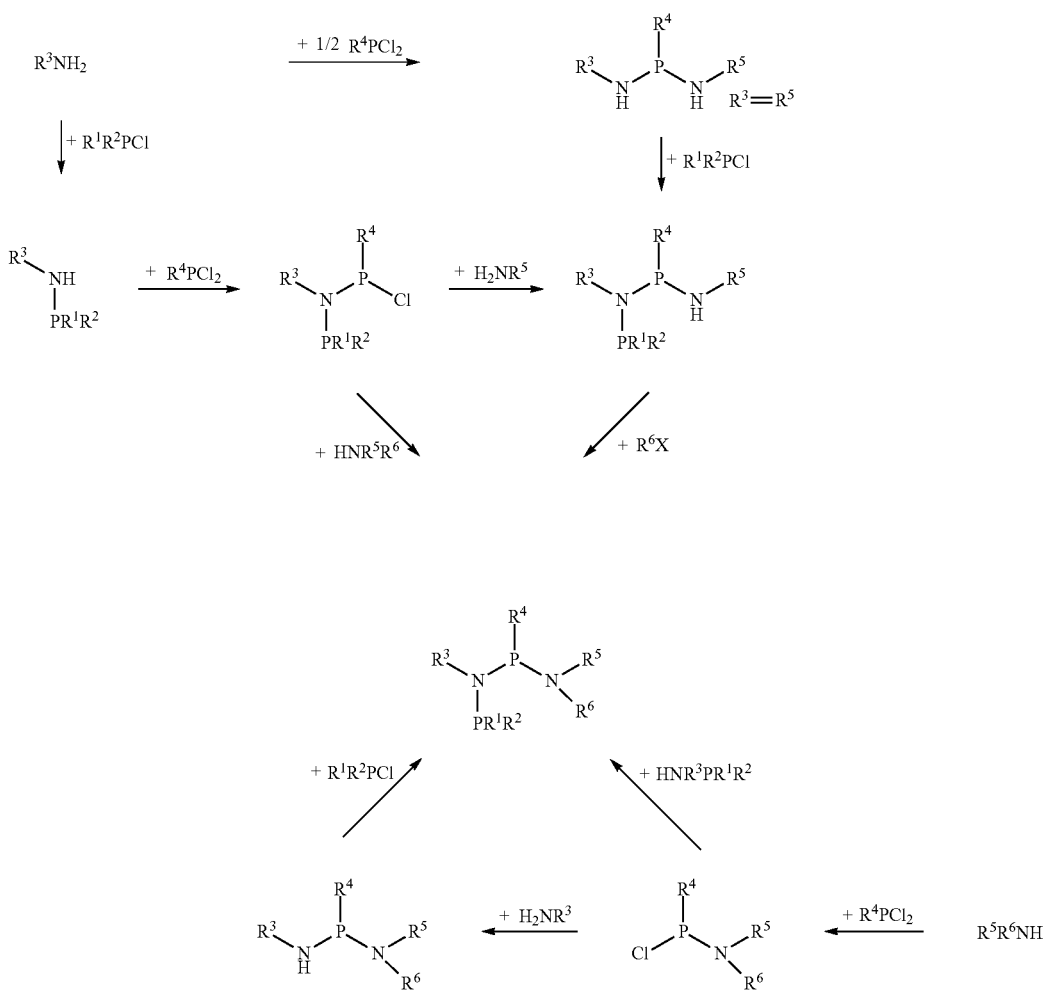

-continued

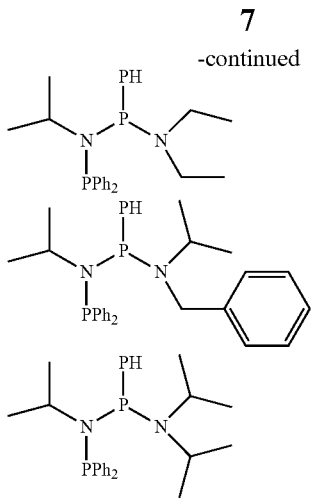

General Procedure for the Preparation of Ph$_2$PN(i-Pr)P(Ph)NR$^1$R$^2$ 2 mmol of the appropriate secondary amine was lithiated with 1.25 mL $^t$BuLi (1.6 M in hexane) at 0° C. in toluene and stirred for 4 hours at room temperature (r.t.). Afterwards the solution of the lithiated amine was transferred to a solution of 0.77 g (2 mmol) Ph$_2$PN($^i$Pr)P(Ph)Cl in toluene at 0° C. and stirred for 24 hours at r.t. The solution was filtrated and evaporated to dryness, remaining an oil or solid, which was washed with cold n-pentane.

In all cases, the preparation of Ph$_2$P($^i$Pr)NPCl was performed as given in: Cross R. J.; Green, H. T.; Keat, R. *J. Chem. Soc. Dalton Trans.* 1976, 1424-1428.

Preparation of Ph$_2$PN(i-Pr)P(Ph)NMe$_2$ (1)

0.77 g (2 mmol) Ph$_2$P($^i$Pr)NPCl, dissolved in toluene, was slowly transferred into a mixture of 10 mL dimethylamine (2M in THF) and toluene at 0° C. The solution was stirred for 12 hour (h) at room temperature whereupon it became cloudy. After evaporation of all volatile compounds, the residue was dissolved in hot n-hexane and filtrated. While resting at −40° C., white crystals of pure Ph$_2$PN($^i$Pr)P(Ph)NMe$_2$ precipitated from the solution ($^{31}$P-NMR C$_6$D6: 48.0; 91.0 ppm broad signals).

For example, the following additional ligands were synthesized using this method.

Ph$_2$PN(i-Pr)P(Ph)N(i-Pr)Ph    (2)

Ph$_2$PN(i-Pr)P(Ph)N(Me)C$_6$H$_{11}$    (3)

Oligomerization Examples

A standard ethylene oligomerization was carried out. A 300 ml pressure reactor, equipped with dip tube, thermowell, gas entrainment stirrer, cooling coil, control units for temperature, pressure, and stirrer speed (all hooked up to a data acquisition system) was inertized with dry argon. The isobaric ethylene supply was maintained by an aluminum pressurized gas cylinder on a balance to monitor the ethylene consumption over time by means of a computerized data acquisition system.

Before conducting an experiment, the reactor was heated to 100° C. at reduced pressure for several hours to eliminate traces of water, oxygen and oxygenated impurities.

For the catalyst preparation, the suitable amounts of the ligands and chromium precursor were weighed in and charged to a Schlenk tube under inert atmosphere. A volume of 75 ml anhydrous solvent was added and the solution was stirred by means of a magnetic stirrer. After dissolving the Cr-compound and ligand, 5 ml of a solution of MMAO-3A (7 wt % Al in heptane) was added. The solution was immediately transferred to the reactor and the reaction was started. The reaction was stopped either when the maximum uptake of ethylene (80 g) was reached or after a set time by closing the ethylene inlet valve, cooling to room temperature, depressurising and opening the reactor.

The liquid product mixture was quenched with diluted HCl and analysed using gas chromatography with a known amount of dodecahydrotriphenylene as internal standard. The solids were filtered, dried and weighed.

The results of the catalytic performance tests are shown in Table 1. In particular, Table 1 shows the results of catalytic tests using ligands of the PNPN(R')(R'') type, where the standard reaction conditions were: $p_{ethylene}$=30 bar, T=60° C., co-catalyst=5 mL MMAO-3A (7 wt % Al in heptane, approx. composition [(CH$_3$)$_{0.7}$(iC$_4$H$_9$)$_{0.3}$AlO]$_n$), 75 mL solvent, [Cr]=0.034 mmol, [Ligand]/[Cr]=1.25 mol/mol.

TABLE 1

| Ligand | solvent | t in min | g products | g solids | C4 | C6 (1-C6) | C8 (1-C8) | C10+ |
|---|---|---|---|---|---|---|---|---|
| 1 | C$_6$H$_5$Cl | 40 | 80 | 5.4 | 1.0 | 40.2 (95) | 44.0 (99.3) | 14.8 |
| 1 | toluene | 55 | 42 | 1.9 | 1.6 | 34.7 (93.6) | 53.8 (99.3) | 9.9 |
| 2 | C$_6$H$_5$Cl | 35 | 80 | 0.15 | 0.9 | 71.7 (97.6) | 13.5 (99.3) | 13.9 |
| 3* | C$_6$H$_5$Cl | 15 | 80 | traces | 0.8 | 50.1 (96.5) | 34.1 (99.4) | 15 |
| 3* | toluene | 50 | 80 | 0.08 | 0.8 | 38.8 (95.5) | 47.9 (99.4) | 12.5 |
| 3** | C$_6$H$_5$Cl | 35 | 80 | 1.9 | 0.9 | 45.8 (92.6) | 37.6 (99.1) | 15.7 |

C4, C6, C8, C10+ wt % in the liquid fraction;
*Cr: 0.015 mmol;
**6.25 mL MAO (10 wt % in toluene)
**The MMAO-3A was replaced by regular, i.e. non-modified, MAO.

The values in the columns of C4, C6, C8 and C10+ are the respective yields in weight percent. The values in brackets in these columns are the respective selectivities (in weight percent) of the C6 or C8 fraction, respectively. For example, in Table 1, for Ligand 1, the C8 column means that the product from the reaction contains 44.0 weight percent C8, wherein 99.3 weight percent of this C8 fraction consists of 1-octene.

The results show that the homogeneous catalyst systems formed showed favorable selectivities to 1-hexene and 1-octene, where the C6/C8 ratio can be adjusted by the nature of the substituents on the terminal N and preferably by the solvent.

According to the second embodiment, ligands according to structure (B) were used.

Ligands of the following structure were, amongst others, synthesized:

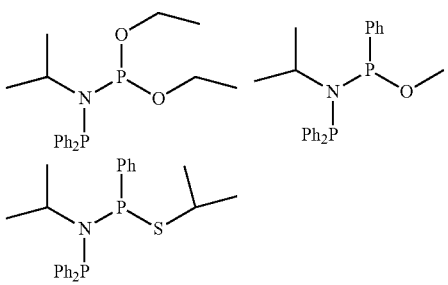

Preparation details of some ligands of the second embodiment are as follows.

Synthesis of the PNP(OR)/PNP(SR)-Ligands:

Preparation of Ph$_2$PN($^i$Pr)P(Ph)S($^i$Pr) (A)

0.77 g (2 mmol) Ph$_2$P($^i$Pr)NPCl, dissolved in toluene, was slowly transferred into a mixture of 0.381 g (5 mmol) 2-propanethiol, 1 mL (7 mmol) triethylamine and toluene at r.t. The solution was stirred for 24 hrs at 40° C., whereupon it became cloudy. After filtration and evaporation of all volatile compounds a colorless oil remained. ($^{31}$P-NMR C$_6$D6: 46.4 ppm broad; 91.7 ppm d; J=26 Hz)

Preparation of Ph$_2$PN($^i$Pr)P(Ph)OEt (B)

A mixture of 0.77 g (2 mmol) Ph$_2$P($^i$Pr)NPCl, 1 mL (7 mmol) triethylamine, 0.233 mL (4 mmol) ethanol and toluene was stirred at 50° C. for 6 days. The turbid solution was filtrated and evaporated to dryness to yield a colorless oil. ($^{31}$P-NMR CDCl$_3$: 39.5 ppm broad; 129.7 ppm d, J=20.6 Hz)

Preparation of Ph$_2$PN($^i$Pr)P(Ph)OMe (C)

A mixture of 0.77 g (2 mmol) Ph$_2$PN($^i$Pr)P(Ph)Cl, 1 mL (7 mmol) triethylamine, 0.162 mL (4 mmol) methanol and toluene was stirred at 50° C. for 2 days. The turbid solution was filtrated and evaporated to dryness to yield a colorless oil. ($^{31}$P-NMR CDCl$_3$: 36.3 ppm broad; 133.3 ppm d, J=19.6 Hz)

The preparation of Ph$_2$P($^i$Pr)NPCl was performed according to: Cross R. J.; Green, H. T.; Keat, R. *J. Chem. Soc. Dalton Trans.* 1976, 1424-1428.

The catalytic oligomerization tests were carried out following the experimental procedure described above.

The results of the catalytic performance tests are shown in Table 2. The homogeneous catalyst systems showed favorable selectivities to 1-hexene and 1-octene. In Table 2, standard reaction conditions are: p$_{ethylene}$=30 bar, T=60° C., co-catalyst=5 mL MMAO-3A (7 wt % Al in heptane), 75 mL solvent, [Cr]=0.034 mmol, [Ligand[/[Cr]=1.25.

TABLE 2

| Ligand | solvent | t in min | g products | g solids | C4 | C6 (1-C6) | C8 (1-C8) | C10+ |
|---|---|---|---|---|---|---|---|---|
| A | C$_6$H$_5$Cl | 60 | 18 | 1.65 | 1.1 | 38.4 (90) | 47.6 (99) | 12.9 |
| B | C$_6$H$_5$Cl | 55 | 80 | 4.7 | 1.3 | 45.0 (92.3) | 39.6 (98.9) | 15.1 |
| B* | C$_6$H$_5$Cl | 35 | 80 | 7.5 | 0.9 | 45.8 (92.5) | 37.6 (99.1) | 15.7 |
| C | C$_6$H$_5$Cl | 50 | 80 | 3.5 | 1.2 | 40.0 (86.5) | 44.9 (98.8) | 13.9 |
| C* | C$_6$H$_5$Cl | 50 | 80 | 7.0 | 1.4 | 36.4 (86.2) | 46.5 (99) | 15.6 |

C4, C6, C8, C10+ wt % in the liquid fraction;
*6.25 mL MAO (10 wt % in toluene)
*MMAO-3A has been replaced by regular, i.e., non-modified, MAO.

In summary, a catalyst composition comprises: (a) a chromium compound, preferably wherein the chromium compound is an organic or inorganic salt, a coordination complex, or an organometallic complexes of Cr(II) or Cr(III), or more preferably CrCl$_3$(THF)$_3$, Cr(III)acetylacetonate, Cr(III)octanoate, chromium hexacarbonyl, Cr(III)-2-ethylhexanoate, (benzene)tricarbonyl-chromium, or a combination comprising at least one of the foregoing; (b) a ligand of the general structure

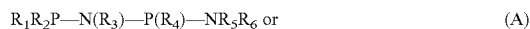

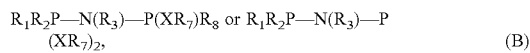

wherein X=O or S and R$_1$, R$_2$, R$_3$, R$_4$, R$_5$, R$_6$, R$_7$ and R$_8$ are independently C$_1$-C$_{10}$-alkyl, C$_6$-C$_{20}$-aryl, C$_3$-C$_{10}$-Cycloalkyl, aralkyl, alkylaryl, or trialkylsilyl, or any cyclic derivatives of (A) and (B), wherein at least one of the P or N atoms of the PNPN-unit or PNP-unit is a member of the ring system, the ring system being formed from one or more constituent compounds of structures (A) or (B) by substitution, preferably wherein R$_1$, R$_2$, R$_3$, R$_4$, R$_5$, R$_6$, R$_7$ and R$_8$ are methyl, ethyl, isopropyl, tert-butyl, cyclohexyl, phenyl, benzyl, tolyl, or xylyl; and (c) an activator or co-catalyst, preferably wherein the activator or co-catalyst is trimethylaluminum, triethylaluminum, triisopropylaluminum, triisobutylaluminum, ethylaluminumsesquichloride, diethylaluminum chloride, ethylaluminumdichloride, methylaluminoxane (MAO), modified methylaminoxane (MMAO), or a combination comprising at least one of the foregoing; and more preferably wherein the ligand (A) is Ph$_2$P—N(i-Pr)—P(Ph)-N(i-Pr)Ph, Ph$_2$P—N(i-Pr)—P(Ph)-N(Me)C$_6$H$_6$, Ph$_2$P—N(i-Pr)—P(Ph)S(i-Pr), Ph$_2$P—N(i-Pr)—P(Ph)OC$_2$H$_5$, Ph$_2$P—N(i-Pr)P(Ph)OCH$_3$, or a combination comprising at least one of the foregoing; optionally wherein one or more of the following conditions applies: the catalyst composition additionally comprises a solvent, preferably an aromatic hydrocarbon, straight-chain aliphatic hydrocarbon, cyclic aliphatic hydrocarbon, straight-chain olefin, straight-chain ether, or a combination comprising at least one of the foregoing, more preferably toluene, benzene, ethylbenzene, cumene, xylenes, mesitylene, hexane, octane, cyclohexane, methylcyclohexane, hexene, heptene, octene, diethylether, tetrahydrofuran, chlorobenzene, or a combination comprising at least one of the foregoing, and most preferably toluene or chlorobenzene; the concentration of the chromium compound is from 0.01 to 100 mmol/l, preferably 0.1 to 10 mmol/l; the ligand/Cr molar ratio is from 0.5 to 50, preferably 0.8 to 2.0; and the Al/Cr molar ratio is from 1:1 to 1000:1, preferably 10:1 to 200:1.

A process for the manufacture of the foregoing catalyst composition comprises combining: a) a chromium compound, preferably wherein the chromium compound is an organic or inorganic salt, a coordination complex, or an organometallic complexes of Cr(II) or Cr(III), or more preferably CrCl$_3$(THF)$_3$, Cr(III)acetylacetonate, Cr(III)octanoate, chromium hexacarbonyl, Cr(III)-2-ethylhexanoate, (benzene)tricarbonyl-chromium, or a combination comprising at least one of the foregoing; (b) a ligand of the general structure

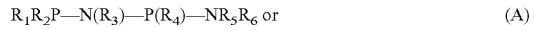

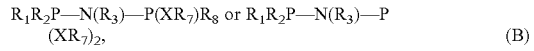

wherein X=O or S and R$_1$, R$_2$, R$_3$, R$_4$, R$_5$, R$_6$, R$_7$ and R$_8$ are independently C$_1$-C$_{10}$-alkyl, C$_6$-C$_{20}$-aryl, C$_3$-C$_{10}$-Cycloalkyl, aralkyl, alkylaryl, or trialkylsilyl, or any cyclic derivatives of (A), or (B), wherein at least one of the P or N atoms of the PNPN-unit or PNP-unit is a member of the ring system, the ring system being formed from one or more constituent compounds of structures (A) or (B) by substitution, preferably wherein R$_1$, R$_2$, R$_3$, R$_4$, R$_5$, R$_6$, R$_7$, or R$_8$ are methyl, ethyl, isopropyl, tert-butyl, cyclohexyl, phenyl, benzyl, tolyl, xylyl, or a combination comprising at least one of the foregoing; and (c) an activator or co-catalyst, preferably wherein the activator or co-catalyst is trimethylaluminum, triethylaluminum, triisopropylaluminum, triisobutylaluminum, ethylaluminumsesquichloride, diethylaluminum chloride, ethylaluminumdichloride, methylaluminoxane (MAO), modified methylaminoxane (MMAO), or a combination comprising at least one of the foregoing; more preferably wherein the ligand (A) is Ph₂P—N(i-Pr)—P(Ph)-N(i-Pr)Ph, Ph₂P—N(i-Pr)—P(Ph)-N(Me)C₆H₆, Ph₂P—N(i-Pr)—P(Ph)S(i-Pr), Ph₂P—N(i-Pr)—P(Ph)OC₂H₅, Ph₂P—N(i-Pr)P(Ph)OCH₃, or a combination comprising at least one of the foregoing; optionally wherein one or more of the following conditions applies: a solvent is optionally combined, preferably an aromatic hydrocarbon, straight-chain, or cyclic aliphatic hydrocarbon, straight-chain olefin, straight-chain ether, or a combination comprising at least one of the foregoing more preferably toluene, benzene, ethylbenzene, cumene, xylenes, mesitylene, hexane, octane, cyclohexane, methylcyclohexane, hexene, heptene, octene, diethylether, tetrahydrofuran, chlorobenzene, or a combination comprising at least one of the foregoing, and most preferably toluene or chlorobenzene; the concentration of the chromium compound is from 0.01 to 100 mmol/l, preferably 0.1 to 10 mmol/l; the ligand/Cr molar ratio is from 0.5 to 50, preferably 0.8 to 2.0; and the Al/Cr molar ratio is from 1:1 to 1000:1, preferably 10:1 to 200:1.

A process for tri- and/or tetramerization of ethylene, comprises subjecting a catalyst composition to a gas phase of ethylene in a reactor and conducting an oligomerization, wherein the catalyst composition comprises a) a chromium compound, preferably wherein the chromium compound is an organic or inorganic salt, a coordination complex, or an organometallic complexes of Cr(II) or Cr(III), or more preferably CrCl₃(THF)₃, Cr(III)acetylacetonate, Cr(III)octanoate, chromium hexacarbonyl, Cr(III)-2-ethylhexanoate, (benzene)tricarbonyl-chromium, or a combination comprising at least one of the foregoing; (b) a ligand of the general structure

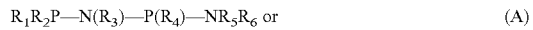
R₁R₂P—N(R₃)—P(R₄)—NR₅R₆ or  (A)

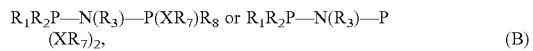
R₁R₂P—N(R₃)—P(XR₇)R₈ or R₁R₂P—N(R₃)—P(XR₇)₂,  (B)

wherein X=O or S and R₁, R₂, R₃, R₄, R₅, R₆, R₇ and R₈ are independently C₁-C₁₀-alkyl, C₆-C₂₀-aryl, C₃-C₁₀-Cycloalkyl, aralkyl, alkylaryl, or trialkylsilyl, or any cyclic derivatives of (A) and (B), wherein at least one of the P or N atoms of the PNPN-unit or PNP-unit is a member of the ring system, the ring system being formed from one or more constituent compounds of structures (A) or (B) by substitution, preferably wherein R₁, R₂, R₃, R₄, R₅, R₆, R₇ and R₈ are methyl, ethyl, isopropyl, tert-butyl, cyclohexyl, phenyl, benzyl, tolyl, xylyl, or a combination comprising at least one of the foregoing; and (c) an activator or co-catalyst, preferably wherein the activator or co-catalyst is trimethylaluminum, triethylaluminum, triisopropylaluminum, triisobutylaluminum, ethylaluminumsesquichloride, diethylaluminum chloride, ethylaluminumdichloride, methylaluminoxane (MAO), modified methylaminoxane (MMAO), or a combination comprising at least one of the foregoing; and more preferably wherein the ligand (A) is Ph₂P—N(i-Pr)—P(Ph)-N(i-Pr)Ph, Ph₂P—N(i-Pr)—P(Ph)-N(Me)C₆H₆, Ph₂P—N(i-Pr)—P(Ph)S(i-Pr), Ph₂P—N(i-Pr)—P(Ph)OC₂H₅, or Ph₂P—N(i-Pr)P(Ph)OCH₃, or a combination comprising at least one of the foregoing; optionally wherein one or more of the following conditions applies: the catalyst composition additionally comprises a solvent, preferably an aromatic hydrocarbon, straight-chain and cyclic aliphatic hydrocarbon, straight-chain olefin, straight-chain ether, or a combination comprising at least one of the foregoing, more preferably toluene, benzene, ethylbenzene, cumene, xylenes, mesitylene, hexane, octane, cyclohexane, methylcyclohexane, hexene, heptene, octene, diethylether, tetrahydrofuran, chlorobenzene, or a combination comprising at least one of the foregoing, and most preferably toluene or chlorobenzene; the concentration of the chromium compound is from 0.01 to 100 mmol/l, preferably 0.1 to 10 mmol/l; the ligand/Cr molar ratio is from 0.5 to 50, preferably 0.8 to 2.0; and the Al/Cr molar ratio is from 1:1 to 1000:1, preferably 10:1 to 200:1; the oligomerization is carried out at a pressure of 1 to 200 bar, preferably 10 to 50 bar; the oligomerization is carried out at a temperature of from 10 to 200° C., preferably 20 to 100° C.; and the mean residence time is from 10 minutes to 20 hours, preferably 1 to 4 hours during oligomerization.

The singular forms "a", "an", and "the" include plural referents unless the context clearly dictates otherwise. "Or" means "and/or". The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. Unless defined otherwise, technical and scientific terms used herein have the same meaning as is commonly understood by one of skill in the art to which this invention belongs. A "combination" is inclusive of blends, mixtures, alloys, reaction products, and the like.

As used herein, the term "hydrocarbyl" and "hydrocarbon" refers broadly to a substituent comprising carbon and hydrogen, optionally with 1 to 3 heteroatoms, for example, oxygen, nitrogen, halogen, silicon, sulfur, or a combination thereof; "alkyl" refers to a straight or branched chain, saturated monovalent hydrocarbon group; "alkylene" refers to a straight or branched chain, saturated, divalent hydrocarbon group; "alkylidene" refers to a straight or branched chain, saturated divalent hydrocarbon group, with both valences on a single common carbon atom; "alkenyl" refers to a straight or branched chain monovalent hydrocarbon group having at least two carbons joined by a carbon-carbon double bond; "cycloalkyl" refers to a non-aromatic monovalent monocyclic or multicylic hydrocarbon group having at least three carbon atoms, "cycloalkenyl" refers to a non-aromatic cyclic divalent hydrocarbon group having at least three carbon atoms, with at least one degree of unsaturation; "aryl" refers to an aromatic monovalent group containing only carbon in the aromatic ring or rings; "arylene" refers to an aromatic divalent group containing only carbon in the aromatic ring or rings; "alkylaryl" refers to an aryl group that has been substituted with an alkyl group as defined above, with 4-methylphenyl being an exemplary alkylaryl group; "arylalkyl" refers to an alkyl group that has been substituted with an aryl group as defined above, with benzyl being an exemplary arylalkyl group; "acyl" refers to an alkyl group as defined above with the indicated number of carbon atoms attached through a carbonyl carbon bridge (—C(=O)—); "alkoxy" refers to an alkyl group as defined above with the indicated number of carbon atoms attached through an oxygen bridge (—O—); and "aryloxy" refers to an aryl group as defined above with the indicated number of carbon atoms attached through an oxygen bridge (—O—).

Unless otherwise indicated, each of the foregoing groups can be unsubstituted or substituted, provided that the substitution does not significantly adversely affect synthesis, stability, or use of the compound. The term "substituted" as used herein means that at least one hydrogen on the designated atom or group is replaced with another group, provided that the designated atom's normal valence is not exceeded. When the substituent is oxo (i.e., =O), then two hydrogens on the atom are replaced. Combinations of substituents and/or variables are permissible provided that the substitutions do not significantly adversely affect synthesis or use of the compound. Exemplary groups that can be present on a "substituted" position include, but are not limited to, cyano; hydroxyl; nitro; azido; alkanoyl (such as a $C_{2-6}$ alkanoyl group such as acyl); carboxamido; $C_{1-6}$ or $C_{1-3}$ alkyl, cycloalkyl, alkenyl, and alkynyl (including groups having at least one unsaturated linkages and from 2 to 8, or 2 to 6 carbon atoms); $C_1$-6 or $C_{1-3}$ alkoxys; $C_{6-10}$ aryloxy such as phenoxy; $C_{1-6}$ alkylthio; $C_{1-6}$ or $C_{1-3}$ alkylsulfinyl; $C_{1-6}$ or $C_{1-3}$ alkylsulfonyl; aminodi($C_{1-6}$ or $C_{1-3}$) alkyl; $C_{6-12}$ aryl having at least one aromatic rings (e.g., phenyl, biphenyl, naphthyl, or the like, each ring either substituted or unsubstituted aromatic); $C_{7-19}$ arylalkyl having 1 to 3 separate or fused rings and from 6 to 18 ring carbon atoms; or arylalkoxy having 1 to 3 separate or fused rings and from 6 to 18 ring carbon atoms, with benzyloxy being an exemplary arylalkoxy.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

The features disclosed in the foregoing description, in the claims and/or in the accompanying drawings may, both separately and in any combination thereof, be material for realizing the invention in diverse forms thereof.

What is claimed is:

1. A catalyst composition comprising:
   (a) a chromium compound;
   (b) a ligand of the general structure
   (B) $R_1R_2P$—$N(R_3)$—$P(XR_7)R_8$, with X=O or S, wherein $R_1$, $R_2$, $R_3$, and $R_8$ are independently $C_1$-$C_{10}$-alkyl, $C_6$-$C_{20}$-aryl, $C_3$-$C_{10}$-cycloalkyl, arylalkyl, alkylaryl, or trialkylsilyl, or any cyclic derivatives of (B), wherein at least one of the P or N atoms of the PNP-unit is a member of the ring system, the ring system being formed from one or more constituent compounds of structure (B) by substitution, and wherein $R_7$ is $C_1$-$C_{10}$-alkyl, $C_3$-$C_{10}$-cycloalkyl, arylalkyl, or trialkylsilyl; and
   (c) an activator or co-catalyst.

2. The catalyst composition according to claim 1, wherein the chromium compound is an organic salt, an inorganic salt, a coordination complex, an organometallic complex of Cr(0) or Cr(III), or a combination comprising at least one of the foregoing.

3. The catalyst composition according to claim 2, wherein the chromium compound is $CrCl_3(THF)_3$, Cr(III)acetylacetonate, Cr(III)octanoate, chromium hexacarbonyl, Cr(III)-2-ethylhexanoate, (benzene)tricarbonyl-chromium, or a combination comprising at least one of the foregoing.

4. The catalyst composition according to claim 1, wherein $R_1$, $R_2$, $R_3$, $R_7$, and $R_8$ are each independently methyl, ethyl, isopropyl, tert-butyl, cyclohexyl, phenyl, benzyl, tolyl, or xylyl.

5. The catalyst composition according to claim 1, wherein the activator or co-catalyst is trimethylaluminum, triethylaluminum, triisopropylaluminum, triisobutylaluminum, ethylaluminumsesquichloride, diethylaluminum chloride, ethylaluminumdichloride, methylaluminoxane (MAO), modified methylaluminoxane (MMAO), or a combination comprising at least one of the foregoing.

6. The catalyst composition according to claim 5, wherein the Al/Cr molar ratio is from 1:1 to 1000:1.

7. The catalyst composition according to claim 1, wherein the ligand is $Ph_2P$—N(i-Pr)—P(Ph)S(i-Pr), $Ph_2P$—N(i-Pr)—$P(Ph)OC_2H_5$, $Ph_2P$—N(i-Pr)P(Ph)$OCH_3$, or a combination comprising at least one of the foregoing.

8. The catalyst composition according to claim 1, additionally comprising a solvent, wherein the solvent is one of aromatic hydrocarbons, straight-chain aliphatic hydrocarbons, cyclic aliphatic hydrocarbons, straight-chain olefins, ethers, or a combination comprising at least one of the foregoing.

9. The catalyst composition according to claim 8, wherein the concentration of the chromium compound is from 0.01 to 100 mmol/l.

10. The catalyst composition according to claim 1, wherein the ligand/Cr molar ratio is from 0.5 to 50.

11. The catalyst composition of claim 1, wherein $R_7$ is $C_1$-$C_{10}$-alkyl, $C_3$-$C_{10}$-cycloalkyl, unsubstituted arylalkyl, or trialkylsilyl.

12. A catalyst composition, obtainable by combining at least:
   (a) a chromium compound;
   (b) a ligand of the general structure
   (B) $R_1R_2P$—$N(R_3)$—$P(XR_7)R_8$,
   wherein
   X=O or S, and
   $R_1$, $R_2$, $R_3$, and $R_8$ are independently $C_1$-$C_{10}$-alkyl, $C_6$-$C_{20}$-aryl, $C_3$-$C_{10}$-cycloalkyl, arylalkyl, alkylaryl, or trialkylsilyl, or any cyclic derivatives of (B), wherein at least one of the P or N atoms of the PNP-unit is a member of the ring system, the ring system being formed from one or more constituent compounds of structure (B) by substitution, and wherein $R_7$ is $C_1$-$C_{10}$-alkyl, $C_3$-$C_{10}$-cycloalkyl, arylalkyl, or trialkylsilyl; and
   (c) an activator or co-catalyst.

13. A catalyst composition comprising:
   (a) a chromium compound;
   (b) a ligand of the general structure
   (B) $R_1R_2P$—$N(R_3)$—$P(XR_7)R_8$, with X=O or S, wherein $R_1$, $R_2$, $R_3$, and $R_8$ are independently $C_1$-$C_{10}$-alkyl, unsubstituted $C_6$-$C_{20}$-aryl, $C_3$-$C_{10}$-cycloalkyl, arylalkyl, alkylaryl, or trialkylsilyl, or any cyclic derivatives of (B), wherein at least one of the P or N atoms of the PNP-unit is a member of the ring system, the ring system being formed from one or more constituent compounds of structure (B) by substitution and wherein $R_7$ is $C_1$-$C_{10}$-alkyl, $C_3$-$C_{10}$-cycloalkyl, unsubstituted arylalkyl, or trialkylsilyl; and
   (c) an activator or co-catalyst.

* * * * *